(12) United States Patent
Igoe et al.

(10) Patent No.: US 12,150,668 B2
(45) Date of Patent: Nov. 26, 2024

(54) SINGLE-LOOP OR MULTIPLE-LOOP SNARE AND METHOD OF FORMING SAME

(71) Applicant: Phase One Medical, LLC, Boulder, CO (US)

(72) Inventors: Michael P. Igoe, Sarasota, FL (US); Adrian C. Ravenscroft, Boulder, CO (US)

( * ) Notice: Subject to any disclaimer, the term of this patent is extended or adjusted under 35 U.S.C. 154(b) by 0 days.

(21) Appl. No.: 18/381,925

(22) Filed: Oct. 19, 2023

(65) Prior Publication Data

US 2024/0130757 A1 Apr. 25, 2024
US 2024/0225685 A9 Jul. 11, 2024

Related U.S. Application Data

(60) Provisional application No. 63/417,498, filed on Oct. 19, 2022.

(51) Int. Cl.
*A61B 17/3205* (2006.01)
*A61B 17/00* (2006.01)

(52) U.S. Cl.
CPC .......... *A61B 17/32056* (2013.01); *A61B 2017/00526* (2013.01); *A61B 2017/00681* (2013.01); *A61B 2017/00867* (2013.01); *A61B 2017/00982* (2013.01)

(58) Field of Classification Search
CPC .......... A61B 17/221; A61B 17/32056; A61B 2017/00358; A61B 2017/00526; A61B 2017/00681; A61B 2017/00867; A61B 2017/00982; A61B 2017/22038; A61B 2017/2212
See application file for complete search history.

(56) References Cited

U.S. PATENT DOCUMENTS

| | | | |
|---|---|---|---|
| 6,007,558 A | | 12/1999 | Ravenscroft et al. |
| 6,159,220 A | * | 12/2000 | Gobron ............... A61B 17/221 |
| | | | 606/127 |
| 6,187,025 B1 | * | 2/2001 | Machek ............... A61F 2/0105 |
| | | | 606/200 |

(Continued)

*Primary Examiner* — Mohamed G Gabr
(74) *Attorney, Agent, or Firm* — Pandiscio & Pandiscio (57) ABSTRACT

A method for forming a surgical snare, the method comprising: providing a plurality of filaments; braiding the plurality of filaments together so as to form a braided tubular construct comprising: a proximal tube having an open proximal end, an open distal end, and a proximal tube lumen extending there between; a distal tube having an open proximal end, an open distal end, and a distal tube lumen extending there between; and a loop region disposed between the distal end of the proximal tube and the proximal end of the distal tube, the loop region comprising at least one loop structure, the at least one loop structure comprising at least three of the plurality of filaments braided together; inserting the distal end of the distal tube into the open distal end of the proximal tube and into the proximal tube lumen such that (i) the distal tube is disposed in the proximal tube lumen such that the at least one loop structure extends distally of the distal end of the proximal tube in the form of at least one loop, and (ii) the distal tube lumen extends from a point located distal to the proximal end of the proximal tube to the at least one loop.

28 Claims, 10 Drawing Sheets

(56) References Cited

U.S. PATENT DOCUMENTS

| | | | |
|---|---|---|---|
| 7,491,211 B2* | 2/2009 | Ziegler | A61B 17/221 606/127 |
| 2004/0153118 A1* | 8/2004 | Clubb | D04C 1/02 606/200 |
| 2006/0100544 A1* | 5/2006 | Ayala | A61M 25/0136 600/585 |
| 2012/0323262 A1 | 12/2012 | Ibrahim et al. | |
| 2016/0324636 A1 | 11/2016 | Rourke et al. | |
| 2017/0303948 A1* | 10/2017 | Wallace | A61B 17/32075 |
| 2019/0000624 A1* | 1/2019 | Wilson | A61F 2/2466 |
| 2020/0345396 A1 | 11/2020 | Rickheim et al. | |
| 2021/0298581 A1 | 9/2021 | Binmoeller et al. | |

* cited by examiner

SINGLE-LOOP OR MULTIPLE-LOOP SNARE AND METHOD OF FORMING SAME

REFERENCE TO PENDING PRIOR PATENT APPLICATION

This patent application claims benefit of U.S. Provisional Patent Application Ser. No. 63/417,498, filed Oct. 19, 2022 by Phase One Medical, LLC for UNIVERSAL BRAIDED STRUCTURE TO FORM SINGLE-LOOP OR MULTIPLE-LOOP SNARE.

The above-identified patent application is hereby incorporated herein by reference.

FIELD OF THE INVENTION

This invention relates to medical devices in general, and more particularly to surgical snares and novel methods for manufacturing surgical snares.

BACKGROUND OF THE INVENTION

In recent years, a number of medical devices have been developed which may be used to retrieve and/or manipulate objects inside the cardiovascular system or hollow viscus during a surgical procedure. Such devices are commonly referred to in the art as "snares" or "baskets" (collectively "snares").

Prior art surgical snares are commonly fabricated from shape-memory materials, nickel cobalt alloy (e.g., MP35N), stainless steel, and/or medical grade polymers and elastomers. Prior art surgical snares generally include one or more loops which are joined at their proximal ends to the distal end of a shaft (e.g., a rigid or semi-rigid shaft with sufficient column strength to advance the snare through a tortuous path).

In use, prior art surgical snares are generally configured to be collapsed (e.g., to assume a smaller profile) and passed through the lumen of a catheter which is, in turn, has been inserted into the body of the patient (e.g., into the vasculature of the patient). The catheter is advanced to the desired location inside the body of the patient, and then the snare is moved distally relative to the catheter so that the loop(s) of the snare, no longer confined to the lumen of the catheter, can naturally expand inside the vessel or hollow viscus at the distal end of the catheter.

After the loop(s) of the snare have been advanced distally out of the lumen of the catheter and appropriately expanded, the loop(s) may be used to perform a surgical procedure. By way of example but not limitation, the loop(s) may be advanced over a foreign object, and then, by advancing the catheter distally over the snare shaft, the loop(s) may be constricted to close the loop(s) around the foreign object. Upon capture within the loop(s), the foreign object may be manipulated within the body of the patient or may be removed from the body of the patient entirely, e.g., by retracting the snare and the foreign object captured in the loop(s) proximally, or by capturing the foreign object to between the loop(s) and the distal end of the catheter and withdrawing the catheter proximally, etc.

Minimally-invasive cardiovascular procedures typically begin by establishing safe access to a vein or artery so that surgical tools (e.g., catheters, snares, balloons, etc.) may be advanced endoluminally through the vein or artery. The Seldinger technique is by far the most common technique used to establish safe access to a vein or artery. With the Seldinger technique, the desired vessel (i.e., the vein or artery to be accessed) is first punctured with a sharp hollow needle and a guidewire is advanced distally through the lumen of the hollow needle into the vessel. The needle is then withdrawn proximally relative to the guidewire and removed from the proximal end of the guidewire, leaving the guidewire disposed in the vessel. Once access has been achieved and the guidewire is in place, the guidewire is carefully and skillfully advanced through the vasculature to position the distal end of the guidewire at the target location. The guidewire provides a "monorail" to introduce other medical devices safely and efficiently into the body and to thereafter move the medical devices along the guidewire to the target location.

By way of example but not limitation, a physician may first insert a hemostatic introducer sheath (e.g., a valved catheter) over the guidewire to increase the diameter of the "working channel" through which other medical devices are to be passed into the vessel of the patient (while minimizing blood loss). As this technique is common, many medical devices configured for endoluminal insertion into the body, e.g., stents, grafts, angioplasty balloons, drug delivery catheters, imaging catheters, etc. are configured to accept a guidewire through a central lumen formed in the medical device.

However, prior art snare designs do not comprise a central lumen for accepting a guidewire, thereby forcing the user to remove the guidewire from the introducer sheath/catheter prior to inserting the snare into the introducer sheath/catheter so that there is enough space within the introducer sheath/catheter to receive the snare. And, with prior art snares, once the physician is finished using the snare, the physician must reinsert and reposition the guidewire if additional medical devices are to be passed through the introducer sheath/catheter, thereby greatly increasing procedural risk (e.g., loss of access, guidewire contamination, etc.).

Currently, commercially available snares are fabricated from individual cables (e.g., the En-Snare® surgical snare manufactured by Merit Medical Systems, Inc. of Jordan, UT, USA) or filaments wrapped with a wire coil (e.g., the Amplatz Goose Neck™ surgical snare manufactured by Medtronic plc of Minneapolis, MN, USA) that are joined together at the distal end of a shaft. Fabricating snares with individual cables or filaments wrapped with a wire coil is extremely labor-intensive, and each such snare design (single-loop or multiloop) requires different materials and assembly methods, thereby complicating manufacture of prior art snares.

Thus there is a need for a new and improved surgical snare which comprises a central lumen for receiving a guidewire, and which is less complex to manufacture than prior art surgical snares.

SUMMARY OF THE INVENTION

The present invention comprises the provision and use of a new and improved surgical snare manufactured as a braided tubular braid construct comprising a central lumen for receiving a guidewire.

The unique benefit of forming the snare of the present invention as a tubular braid construct is that all the filaments that comprise the tubular braid are braided together (thereby enhancing mechanical integrity of the snare), and the tubular braid construct, by virtue of being formed as a tube, inherently has a central lumen to facilitate the passage of a guidewire. More particularly, the novel snare of the present invention provides improved mechanical integrity and a structure that can be formed into a single-loop or multi-loop snare, while ultimately significantly reducing the cost associated with the manufacture of the novel snare.

In a preferred form of the invention, there is provided a method for forming a surgical snare, said method comprising:
providing a plurality of filaments;
braiding said plurality of filaments together so as to form
a braided tubular construct comprising:
a proximal tube having an open proximal end, an open distal end, and a proximal tube lumen extending there between;
a distal tube having an open proximal end, an open distal end, and a distal tube lumen extending there between; and
a loop region disposed between said distal end of said proximal tube and said proximal end of said distal tube, said loop region comprising at least one loop structure, said at least one loop structure comprising at least three of said plurality of filaments braided together;
inserting said distal end of said distal tube into said open distal end of said proximal tube and into said proximal tube lumen such that (i) said distal tube is disposed in said proximal tube lumen such that said at least one loop structure extends distally of said distal end of said proximal tube in the form of at least one loop, and (ii) said distal tube lumen extends from a point located distal to said proximal end of said proximal tube to said at least one loop.

In another preferred form of the invention, there is provided a surgical snare comprising:
a braided tubular construct formed by braiding together a plurality of filaments, said braided tubular construct comprising:
a proximal tube having an open proximal end, an open distal end, and a proximal tube lumen extending there between;
a distal tube having an open proximal end, an open distal end, and a distal tube lumen extending therebetween; and
a loop region disposed between said distal end of said proximal tube and said proximal end of said distal tube, said loop region comprising a plurality of solid loop structures, each of said plurality of solid loop structures comprising at least three of said plurality of filaments braided together;
wherein said distal end of said distal tube is inserted into said open distal end of said proximal tube and into said proximal tube lumen such that (i) said distal tube is disposed in said proximal tube lumen and said plurality of solid loop structures extend distally of said distal end of said proximal tube in the form of a plurality of loops, and (ii) said distal tube lumen extends from a point located distal to said proximal end of said proximal tube to said plurality of loops.

In another preferred form of the invention, there is provided a method for forming a surgical snare, said method comprising:
providing twenty-four filaments;
braiding said twenty-four filaments together so as to form
a braided tubular construct comprising:
a proximal tube having an open proximal end, an open distal end, and a proximal tube lumen extending there between;
a distal tube having an open proximal end, an open distal end, and a distal tube lumen extending therebetween; and
a loop region disposed between said distal end of said proximal tube and said proximal end of said distal tube, said loop region comprising three solid loop structures, each of said three solid loop structures comprising eight filaments braided together;
radially constraining said distal tube during braiding of said distal tube such that said distal tube comprises a radius that is less than the radius of said distal tube lumen;
inserting said distal end of said distal tube into said open distal end of said proximal tube and into said proximal tube lumen such that (i) said distal tube is disposed in said proximal tube lumen and said three solid loop structures extend distally of said distal end of said proximal tube in the form of three loops, and (ii) said distal tube lumen extends from a point located distal to said proximal end of said proximal tube to said three loops.

In another preferred form of the invention, there is provided a method for forming a surgical snare, said method comprising:
providing a plurality of filaments;
braiding said plurality of filaments together so as to form
a braided tubular construct comprising:
a proximal tube having an open proximal end, an open distal end, and a proximal tube lumen extending there between;
a distal tube having an open proximal end, an open distal end, and a distal tube lumen extending therebetween; and
a loop region disposed between said distal end of said proximal tube and said proximal end of said distal tube, said loop region comprising a plurality of solid loop structures, each of said plurality of solid loop structures comprising at least three of said plurality of filaments braided together;
rotating at least one of said proximal tube and said distal tube relative to the other of said proximal tube and said distal tube about a central longitudinal axis of said distal tube such that said plurality of solid loop structures are twisted together to form a single solid loop structure;
inserting said distal end of said distal tube into said open distal end of said proximal tube and into said proximal tube lumen such that (i) said distal tube is disposed in said proximal tube lumen and said single solid loop structure extends distally of said distal end of said proximal tube, and (ii) said distal tube lumen extends from a point located distal to said proximal end of said proximal tube to said single solid loop structure.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Traditionally, braiding requires a minimum of three threads/filaments (collectively "filaments") of a specified material (e.g., fabric, metal wire, composites, etc.) which are interlaced in a specific pattern to form a single profile. Braids can be used to form solid three-dimensional objects (e.g., a rod) or hollow three-dimensional objects (e.g., a tube). When forming hollow three-dimensional objects such as tubes, a core material is preferably used, with the braided construct being braided around the core material to create a tubular braided construct. Braids vary greatly from cable or rope in that the interlacing of the threads/filaments are a key feature of the process.

Braiding allows tremendous design/construct flexibility. By way of example but not limitation, a hollow braided construct may be created so as to allow for selected segments of the braided construct to easily change diameter in response to external forces (e.g., to increase in diameter radially as the construct is constricted longitudinally) or have variable diameter (e.g., a plurality of different radial diameters along a longitudinal dimension of the braided construct).

Solid braid constructs may be constructed to have excellent axial compliance while affording bend flexibility. These characteristics are unique to braiding constructs and such characteristics are not provided by cable, rope and coiling.

The present invention is preferably formed using a new braiding technology sometimes hereinafter referred to as "variation braiding". Prior to the introduction of a variation braider, braid machines could construct hollow or solid core braids with various "ends" (i.e., number of filaments), "PIC" count (i.e., density of the braid over a unit of length) and braid angle (for tubular braids, dictating radial strength). Variation braiders allows for a braid construct having segments which are hollow or tubular, which segments can then segment into smaller braided constructs (either tubular segments or solid segments) and then return to a single tubular segment again. Variation braiders also allow for selecting number of ends, PIC count and braid angle for the tubular section with the added benefit of segmenting into multiple variation braid segments.

The number of segments of a braided construct is directly related to the number of ends the braider is configured for. By way of example but not limitation, in a 24-filament configuration the maximum number of segments that can be created are 8, as each segment requires 3 filaments to create a braid. Conversely the variation braider can be configured to have a single tubular section that creates a single variation segment that is solid (i.e., non-tubular) and contains an equal number of filaments. Variation braiding may be used to braid a single tube construct from all of the filaments used which tube then transitions to a plurality of braided segments before again transitioning to a single braided tube construct in a continuous operation (spool-to-spool), as will hereinafter be discussed in further detail.

The present invention comprises the provision and use of a new and improved surgical snare manufactured as a braided tubular braid construct, which novel snare comprises a central lumen for receiving a guidewire.

More particularly, and looking now at FIG. 1, the present invention comprises the provision and use of a new and improved snare 5, and a novel method for forming snare 5 from a braided construct formed using variation braiding, as will hereinafter be discussed in further detail.

Snare 5 generally comprises a braided construct 10 comprising a proximal tube 15, a distal tube 20 and a loop region 25 disposed between proximal tube 15 and distal tube 20. Braided construct 10 is formed as a single construct. That is, proximal tube 15, loop region 25 and distal tube 20 are formed integrally (i.e., braided) as a single braided construct comprising a plurality of filaments braided together to form a three-dimensional structure.

Figure 2:
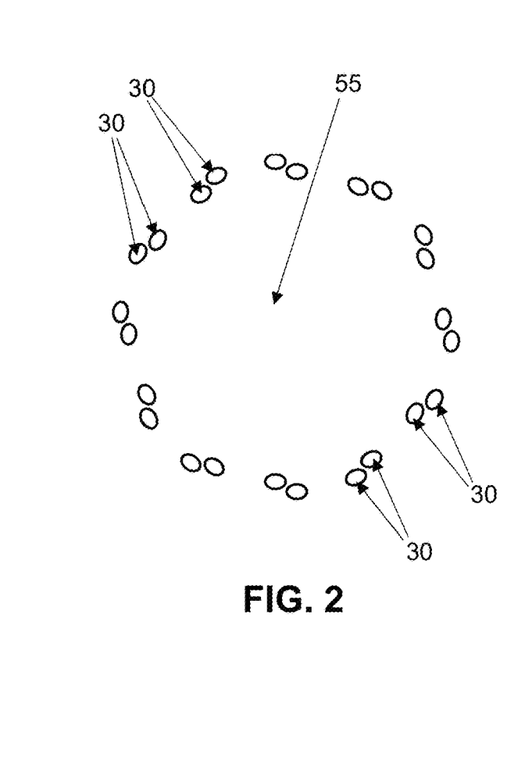
FIG. 2 is a schematic, cross-sectional view of a section of the braided construct of FIG. 1.

Looking now at FIG. 2, braided construct 10 is braided from a plurality of wires or filaments 30. The number of filaments 30 employed to form braided construct 10 typically ranges from 6 filaments to 36 filaments (typically an even number of filaments are employed), with each of the filaments 30 ranging from 0.001 inch to 0.008 inch in diameter. In one preferred form of the invention, twenty-four filaments 30 are used to form braided construct 10.

Still looking at FIG. 2, a predetermined number of filaments 30 (e.g., twenty-four filaments) are braided together using the variation braiding process discussed above, whereby to form proximal tube 15 in the form of a hollow braided structure defining a central proximal lumen 35 (FIG. 2).

Figure 1:
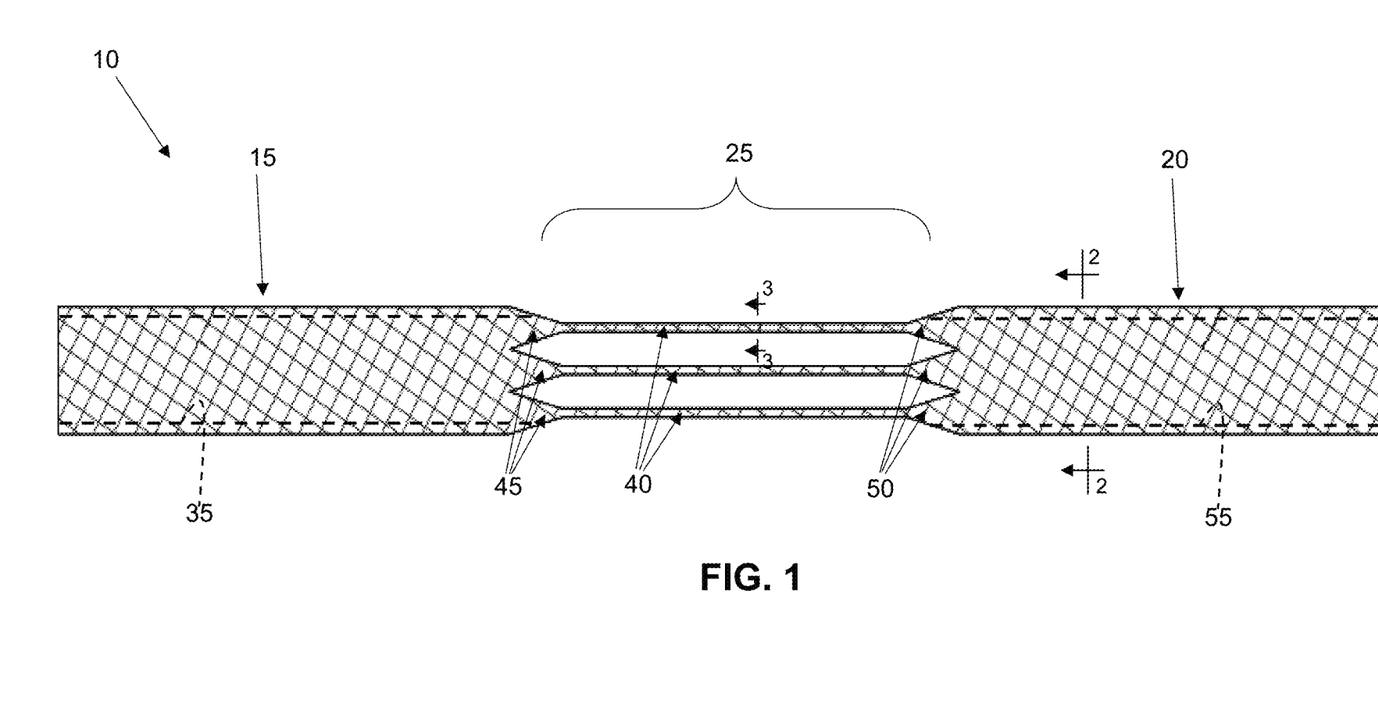
FIG. 1 is a schematic view of a novel braided construct used to form a novel snare.
Figure 3:
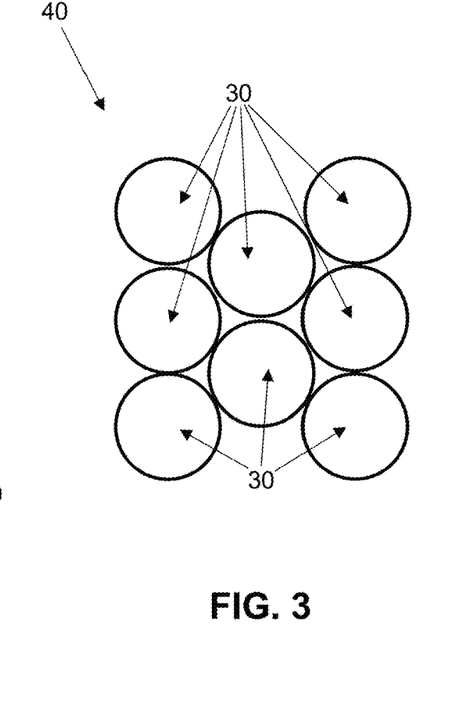
FIG. 3 is a schematic, cross-sectional view of another section of the braided construct of FIG. 1.

Looking now at FIGS. 1 and 3, once proximal tube 15 has been formed so as to have the desired length, filaments 30 transition into a plurality of solid loop structures 40 at proximal transition points 45. Solid loop structures 40 then extend distally a predetermined distance (which is selected according to the size loop desired, see below) before each solid loop structure 40 transitions at distal transition points 50 into distal tube 20. Each solid loop structure 40 comprises a plurality of filaments 30 braided together to form the solid loop structure. By way of example but not limitation, when twenty-four filaments 30 are used to form braided construct 10, each solid loop structure 40 may comprise 8 braided filaments.

It will be appreciated that inasmuch as the number of solid loop structures 40 to be formed determines the number of loops that snare 5 will ultimately comprise, the number of solid loop structures 40 (and hence, the number of filaments 30 comprising the solid loop structures 40) may be varied as desired so as to produce the desired number of loop structures 40. By way of example but not limitation, if four loop structures are desired (i.e., so as to produce a snare 5 comprising four loops), each loop structure 40 comprises six filaments 30. By way of further example but not limitation, if two loop structures are desired (i.e., so as to produce a snare 5 comprising two loops), each loop structure 40 comprises twelve filaments 30. Thus it will be appreciated that the number of filaments 30 comprising each loop structure 40 is a function of the total number of filaments 30 utilized to form braided construct 10 divided by the number of loop structures 40 desired.

It will further be appreciated that the length of each loop structure 40 determines the size (i.e., circumference) of the eventual loops that are formed from each loop structure 40. Thus, by controlling the distance that each loop structure 40 is braided in the distal direction, the eventual size of the resulting loops can be controlled.

Still looking at FIG. 1, moving distally to a predetermined distance from proximal transition point 45, each loop structure 40 transitions at distal transition point 50 into distal tube 20. As each of the loop structures 40 transition at distal transition point 50 into distal tube 20, the filaments 30 comprising each of the loop structures 40 are braided together so as to form the sidewall of distal tube 20, whereby to define a central distal lumen 55.

It will be appreciated that, in one preferred form of the invention, as the plurality of filaments 30 are braided together to form distal tube 20, an external compression sleeve 60 (FIG. 6) is used to radially constrict distal tube 20 during braiding so as to form distal tube 20 with a slightly smaller diameter than the diameter of central proximal lumen 35 of proximal tube 15, whereby to facilitate insertion of distal tube 20 into central proximal lumen 35 of proximal tube 15, as will hereinafter be discussed in further detail.

In addition, if desired, during or after the braiding of braided construct 10, braided construct 10 may be "shape-set" by heat annealing (e.g., soft annealing) the filaments 30 so as to prevent the filaments 30 (and hence, braided structure 10) from unraveling. More particularly, if desired, a two-step heat annealing process may be employed in order to form braided structure 10. In the first "pre-annealing" heat annealing step of the two-step heat annealing process, braided construct 10 may be heat annealed so as to (i) prevent filaments 30 comprising proximal tube 15, distal tube 20 and/or loop region 25 from unraveling, and/or (ii) setting the outer diameter of proximal tube 15 and/or distal tube 20 at the braided outer diameter, whereby to form the proximal tube 15 and/or distal tube 20 with an outer diameter that matches the diameter of a core (not shown) over which proximal tube 15 and/or distal tube 20 are braided. As a result, when the assembled snare 5 is to be heat annealed in final form, proximal tube 15 and/or distal tube 20 will "grip" a mandrel having a slightly larger outer diameter than the diameter of proximal tube 15 and/or distal tube 20 when disposed in central proximal lumen 35 and central distal lumen 55, respectively, whereby to maintain the snare 5 on the mandrel during the final heat annealing process.

Figure 4:
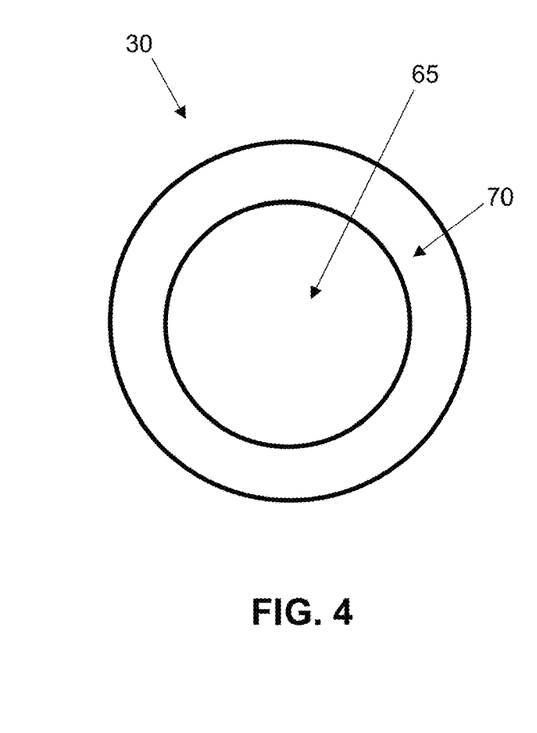
FIG. 4 is a cross-sectional view of a novel composite filament formed in accordance with the present invention.

It will also be appreciated that, If desired, one or more filaments 30 used to form braided construct 10 may comprise a composite of a plurality of materials. By way of example but not limitation, and looking now at FIG. 4, there is shown a composite filament 30 comprising a core material 65 and an outer sheath 70. Core material 65 and/or outer sheath 70 may be selected for desired mechanical properties (e.g., column strength, flexibility, shape memory) and/or radiopacity (e.g., so as to facilitate visualization on fluoroscopy or other imaging modalities). By way of example but not limitation, one or more filaments 30 may be constructed with a Nitinol outer sheath 70 and a noble metal (e.g., gold, platinum, iridium, etc.) core material 65. With this form of the invention, the noble metal core material 65 provides radiopacity and the Nitinol outer sheath 70 provides shape memory (or super elasticity). It will be appreciated that, if desired, the outer sheath 70 may be constructed of radiopaque material and the core material 65 may be made of a non-radiopaque material.

It will also be appreciated that, if desired, braided construct 10 may be formed from filaments 30 having different diameters ranging from 0.001 inch to 0.008 inch. By way of example but not limitation, some of the filaments 30 used to form braided construct 10 may have a diameter of 0.001 inch while others of the filaments used to form braided construct 10 may have a diameter of 0.005 inch. By way of still further example but not limitation, some of the filaments 30 used to form braided construct 10 may have a diameter of 0.001 inch, others of the filaments 30 used to form braided construct 10 may have a diameter of 0.005 inch, and still others of the filaments 30 used to form the braided construct 10 may have a diameter of 0.008 inch.

And it will also be appreciated that braided construct 10 may be braided out a plurality of filaments 30 which are themselves formed from braided or cabled filaments.

It will be appreciated that the continuous (e.g., spool-to-spool) braiding process used to form snare 5 may be employed in order to make a plurality of snares 5 from a single braided construct 10. To that end, in another form of the present invention, braided construct 10 is formed as a continuous series of tubes separated by loop regions. More particularly, and looking now at FIG. 5, with this form of the invention, braided construct 10 comprises two or more loop regions 25 separated by one or more intermediate tube(s) 75. Intermediate tube 75 is braided from filaments 30 in the same manner as distal tube 20, however, filaments 30 transition at second proximal transition points 45*a* at the distal end of intermediate tube 75 into one or more solid loop structures 40*a* defining a second loop region 25*a* before transitioning at distal transition points 50*a* into distal tube 20 in the manner discussed above.

Figure 5:
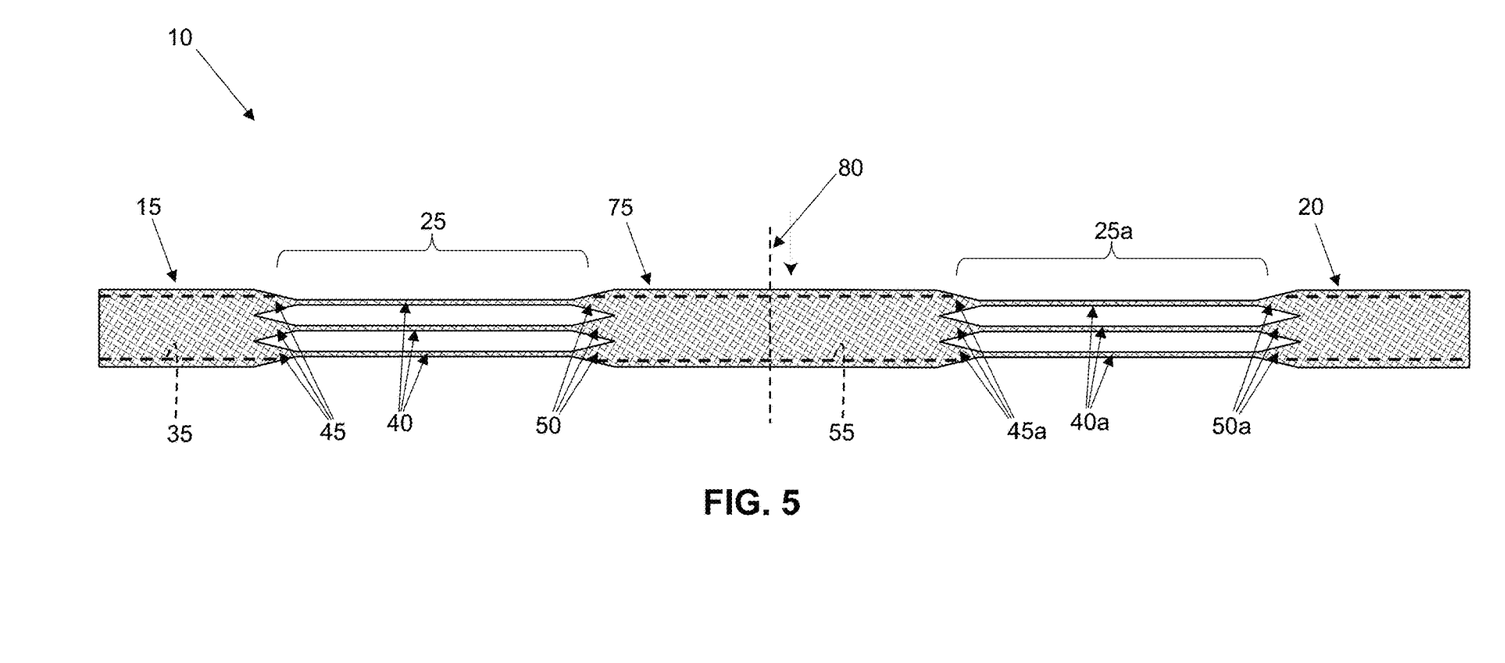
FIG. 5 is a schematic view of another novel braided construct formed in accordance with the present invention.

It will be appreciated that, with this form of the invention, distal tube 20 may be replaced by a second intermediate tube 75*a* which transitions at i"s distal end at a proximal transition points 45*b* into one or more solid loop structures 40*b* defining a third loop region 25*a*, and so on. Each intermediate tube 75 is characterized by a trim location 80 located approximately at the midpoint of each intermediate tube 75. As a result, with this form of the invention, braided construct 10 may be formed with a proximal tube 15 at the proximal end, a distal tube 20 at the distal end, a plurality of intermediate tubes 75, 75a, 75b, etc., and a plurality of loop regions 25, 25a, 25b, etc. disposed therebetween. Braided construct 10 may then be cut at trim region(s) 80 so as to form two or more braided constructs 10, each of which can thereafter be transformed into a snare 5, as will hereinafter be described in further detail. As discussed above with respect to the embodiment of FIG. 1, a two-step heat annealing process (or a three-step heat annealing process) may also be utilized in order to prevent filaments 30 from unraveling and/or to fix the outer diameter of one or more of proximal tube 15, distal tube 20, and/or intermediate tube 75 in order to facilitate forming snare 5, as will hereinafter be discussed in further detail.

Figure 6:
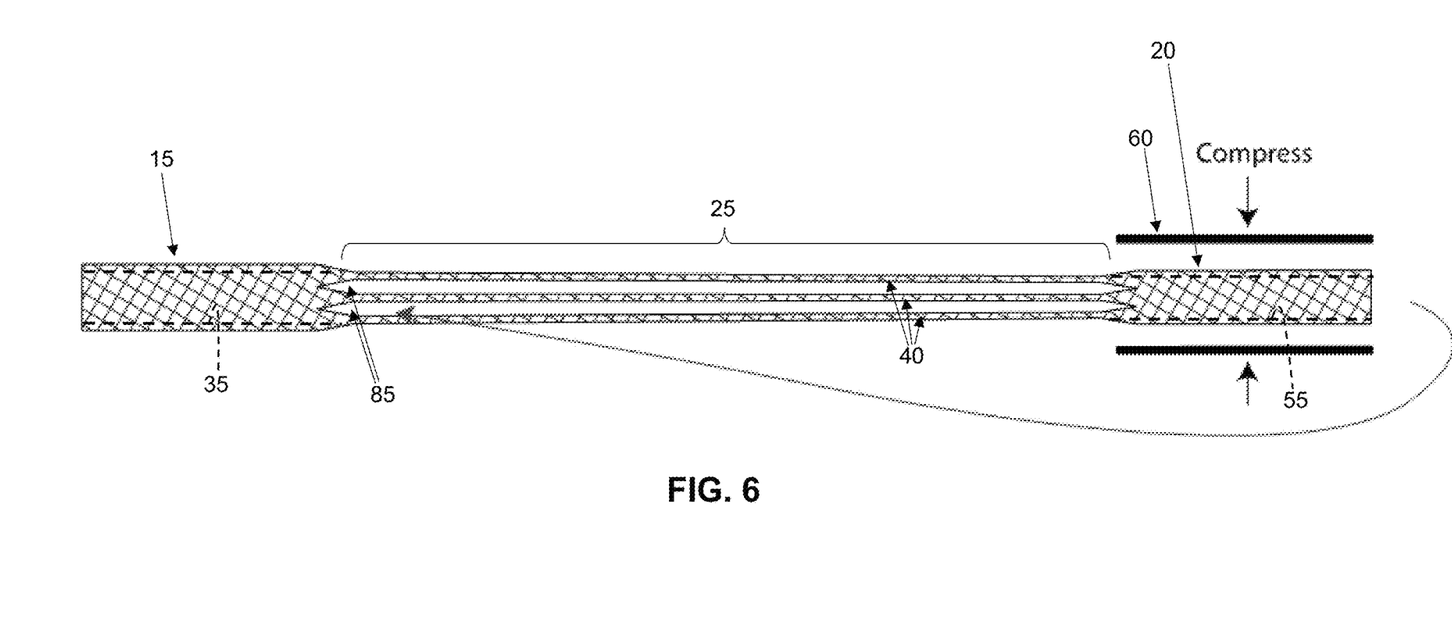
FIG. 6 is a schematic view of still another braided construct formed in accordance with the present invention showing how the braided construct may be made into a novel snare formed in accordance with the present invention.

Looking now at FIG. 6, snare 5 is formed from braided construct 10 by inserting the distal end of distal tube 20 into central proximal lumen 35 of proximal tube 15. More particularly, as discussed above, distal tube 20 is preferably formed so as to comprise a diameter that is slightly less than the diameter of central proximal lumen 35 of proximal tube 15 (e.g., via application of external compression from compression sleeve 60 when forming distal tube 20). To form snare 5, distal tube 20 is passed through a gap 85 between two adjacent solid loop structures 40 of loop region 25, and into the distal end of central proximal lumen 35 of proximal tube 15. Since distal tube 20 has a diameter only slightly smaller than the diameter of central proximal lumen 35 of proximal tube 15, the sidewalls of distal tube 20 are pushed against the inner surface of the sidewalls of proximal tube 15 with substantially no gapping therebetween, such that central distal lumen 55 of distal tube 20 remains open. Where proximal tube 15 and distal tube 20 are constructed so as to have the same longitudinal dimension, the distal end of distal tube 20 will preferably be disposed intermediate the proximal and distal ends of proximal tube 15 once snare 5 has been formed out of braided construct 10 according to the manner discussed above. In one preferred form of the invention, the distal end of distal tube 20 resides in central proximal lumen 35 at a location halfway between the proximal and distal ends of proximal tube 15. And it will be appreciated that, if desired, distal tube 20 may be formed so as to have a length which is approximately half the length of the distance between the proximal and distal ends of proximal tube 15.

In order to facilitate insertion of distal tube 20 into central proximal lumen 35 of proximal tube 15, (i) proximal tube 15 may be formed over a mandrel (not shown) disposed in all (or a portion of) central proximal lumen 35, and/or (ii) distal tube 20 may be formed over a second mandrel (not shown) disposed in all (or a portion of) central lumen 55 of distal tube 20. Heat-annealing (e.g., pre-annealing) braided construct 10 prior to inserting distal tube 20 into central proximal lumen 35 of proximal tube 15 acts to fix the outer diameter of proximal tube 15 and/or distal tube 20 such that proximal tube 15 and/or distal tube 20 grip the mandrels disposed in central proximal lumen 35 and/or central distal lumen 55, whereby to greatly facilitate the insertion of distal tube 20 into central proximal lumen 35 of proximal tube 15 in the manner discussed above.

It will be appreciated that this pre-annealing step is separate from the final heat annealing step that is performed once braided construct 10 has been formed into snare 5. That is, the final heat annealing step sets the geometry (i.e., fixes) filaments 30 in the form of the final desired construct (e.g., snare 5), whereas the "pre-annealing" heat annealing step is utilized in order to change the physical properties of braided construct 10 so as to facilitate the insertion of distal tube 20 into central proximal lumen 35 of proximal tube 15 in the manner discussed above.

Figure 7:
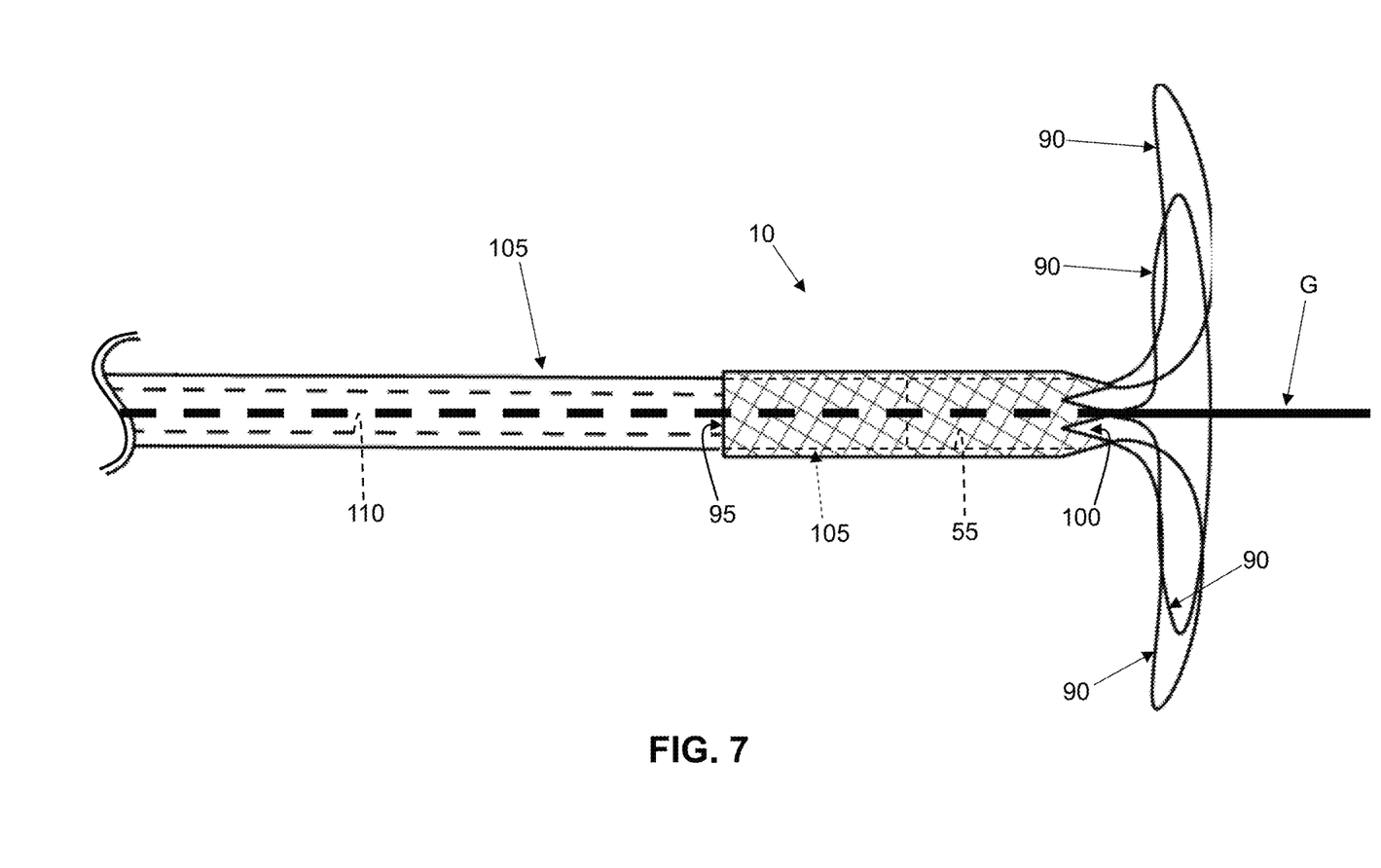
FIG. 7 is a schematic view of a novel snare formed in accordance with the present invention and mounted to a catheter such that a guidewire lumen of the catheter is axially aligned with a guidewire lumen of the novel snare.

Looking now at FIG. 7, once distal tube 20 has been inserted into proximal tube 15 in the manner discussed above, each solid loop structure 40 is transformed into a snare loop 90, and central distal lumen 55 extends entirely through the combined proximal tube 15 and distal tube 20 so as to define a proximal opening 95 and a distal opening 100. More particularly, solid loop structures 40 of loop region 25 are preferably shape-set by heat annealing so as to form snare loops 90 of equal lengths, of equal radial spacing, and preferably so as to extend at an angle of 15° to 90° relative to the central axis of central distal lumen 55, thereby forming a multi-looped snare 5 with central distal lumen 55 extending therethrough to serve as a guidewire lumen, as will hereinafter be discussed in further detail.

Still looking at FIG. 7, if desired, snare 5 may be mounted to the distal end of a single- or multi-lumen catheter 105 (or other tube) such that a central lumen 110 of catheter 105 is axially aligned with central distal lumen 55 of snare 5, whereby to permit snare 5 and catheter 105 to be passed over a guidewire G (FIG. 7) such that guidewire G extends out of distal opening 100 of snare 5. It will be appreciated that, inasmuch as distal tube 20 preferably only extends approximately half of the distance between the distal and proximal ends of proximal tube 15 into central proximal lumen 35 of proximal tube 15 (i.e., such that distal tube 20 occupies the portion of central proximal lumen 35 extending from the central point thereof to the distal end thereof), the proximal portion of central proximal lumen 35 is open to receive the distal end of catheter 105 in order to mount catheter 105 to snare 5, as will hereinafter be discussed in further detail.

Figure 8:
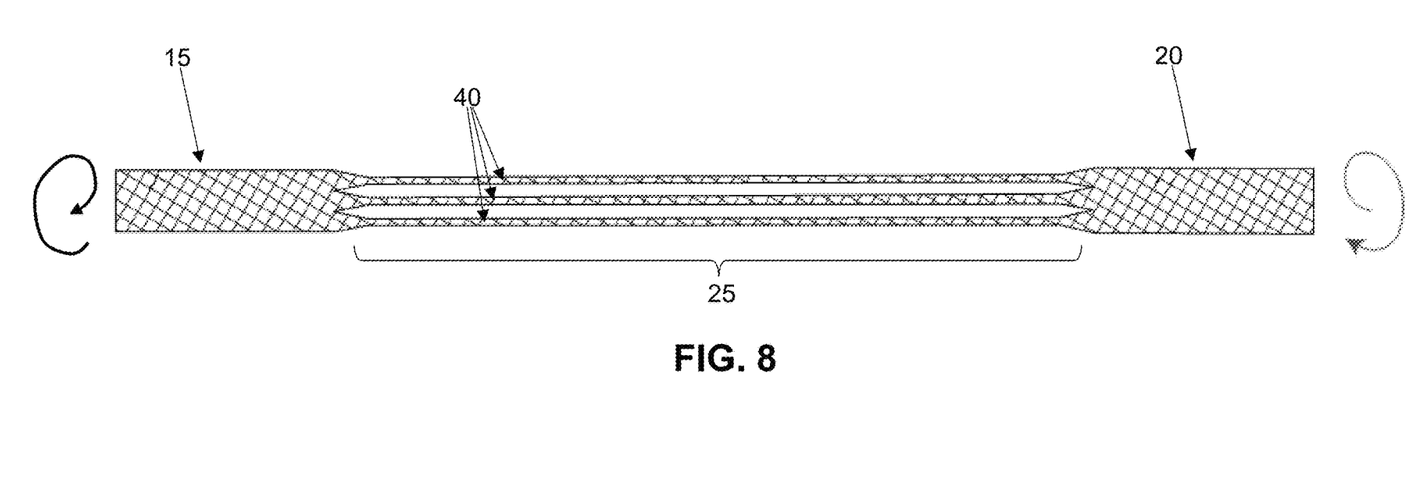
FIG. 8 is a schematic view of a novel braided construct formed in accordance with the present invention, showing how the braided construct may be made into a novel single-loop snare formed in accordance with the present invention.
Figure 9:
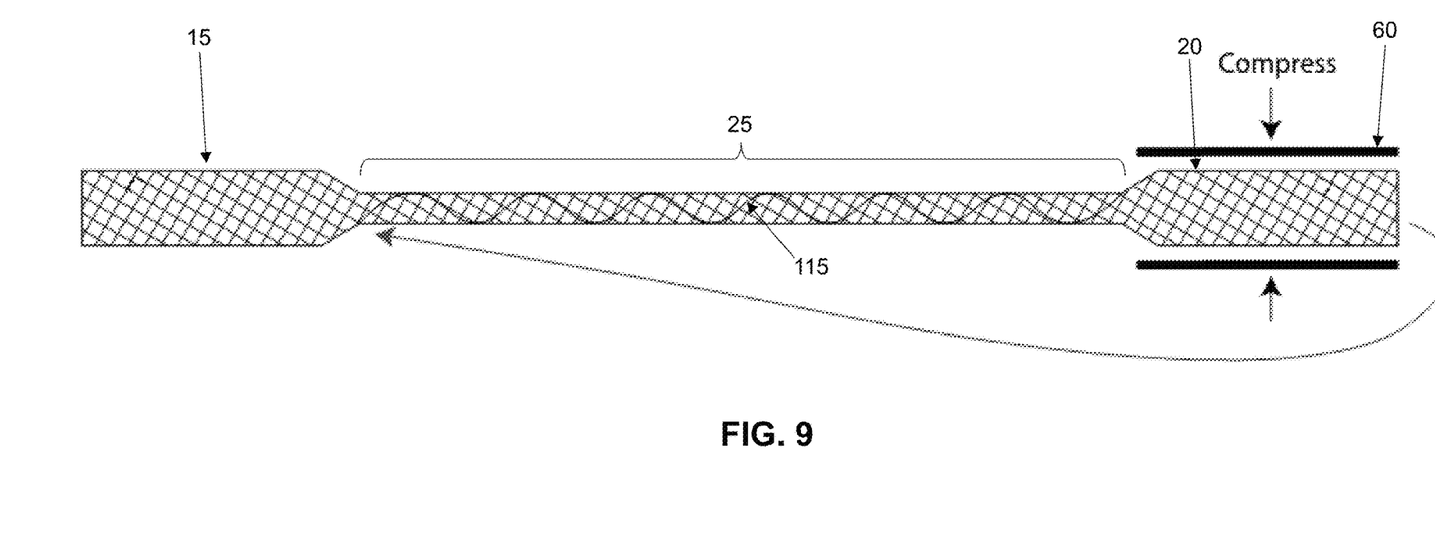
FIG. 9 is a schematic view showing further details of how the novel braided construct of FIG. 8 may be formed into a novel single-loop snare formed in accordance with the present invention.
Figure 10:
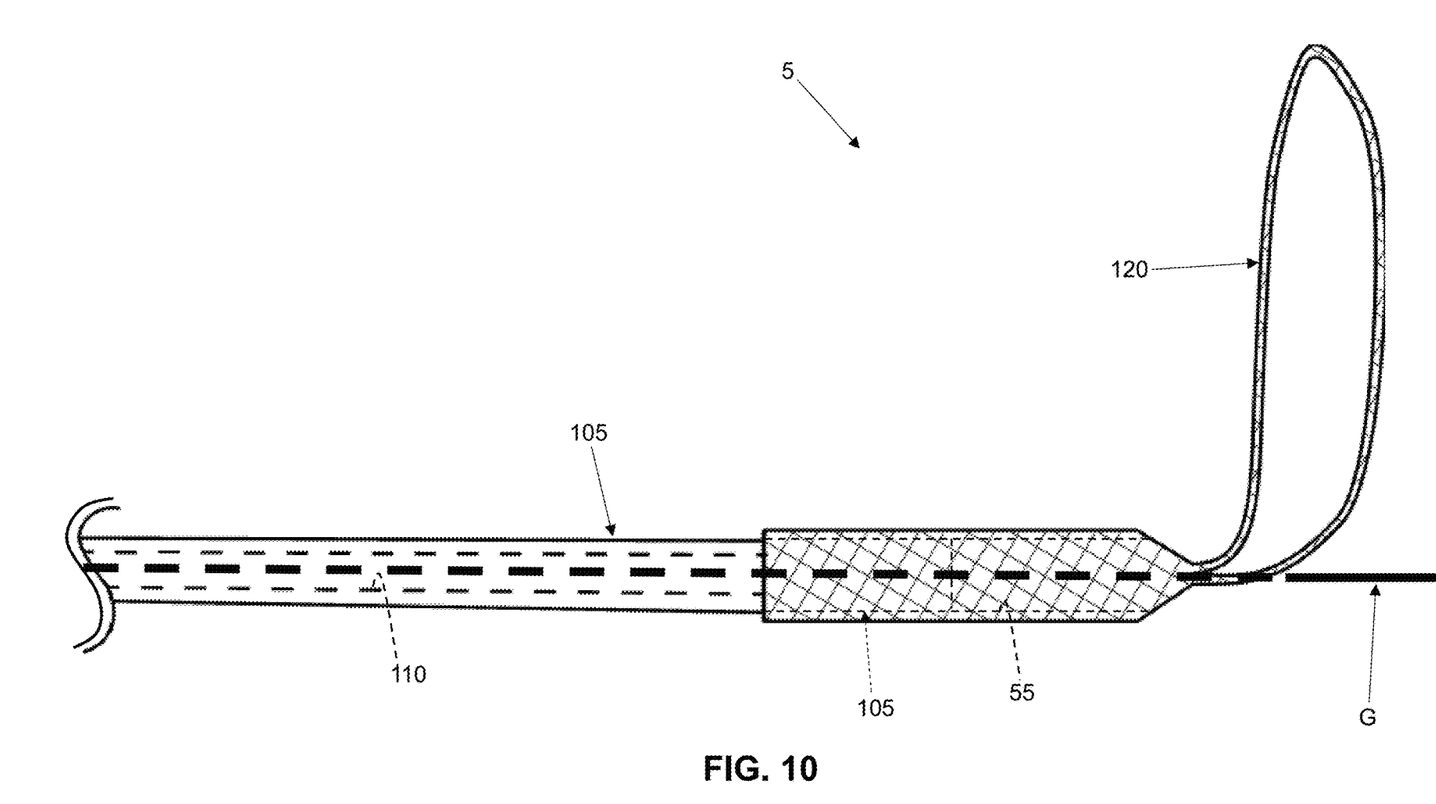
FIG. 10 is a schematic view of a single-loop snare formed from the novel braided construct of FIGS. 8 and 9 mounted to a catheter such that a guidewire lumen of the catheter is axially aligned with a guidewire lumen of the novel snare.

In another embodiment of the present invention, and looking now at FIGS. 8-10, a plurality of loop structures 40 of loop region 25 are twisted together to form a single, combined loop structure 115 (FIG. 9) disposed between proximal tube 15 section and distal tube 20. More particularly, proximal tube 15 and distal tube 20 are rotated in opposite directions (and/or one of proximal tube 15 and distal tube 20 is rotated while the other of proximal tube 15 and distal tube 20 is kept stationary), so as to twist solid loop structures 40 together, whereby to form combined loop structure 115. Solid loop structures 40 are twisted together and shape-set by heat annealing to form a single snare loop 120 extending at 15° to 90° relative to the central longitudinal axis of central distal lumen 55. When the distal end of distal tube 20 section is thereafter inserted into the distal end of central proximal lumen 35 of proximal tube 15 (see above), single snare loop 120 extends distally beyond the distal end of the proximal tube 15, with central distal lumen 55 extending through snare 5 such that a guidewire G may pass through central distal lumen, out of distal opening 100, and distally beyond snare loop 120. It will be appreciated that the embodiment of FIGS. 8-10 may be subjected to a pre-annealing heat annealing step prior to inserting distal tube 20 into central proximal lumen 35 in the same manner as discussed above in connection with the embodiments of FIGS. 1, 5 and 6, in order to facilitate forming snare 5. With the embodiment of FIGS. 8-10, the pre-annealing step is preferably performed before single snare loop 120 is formed by twisting together solid loop structures 40 as discussed above.

It will further be appreciated that the structural properties of single snare loop 120 may be controlled by varying the cross-over positions and timing of the braiding of loop structures 40 from filaments 30, as will be apparent to one of skill in the art in view of the present disclosure.

Snare 5 comprising a single snare loop 120 may then be mounted to single- or multiple-lumen catheter 105 in the manner discussed above. Lumen 110 of catheter 105 is axially aligned with central distal lumen 55 of distal tube 20 so as to provide a pathway for guidewire G (or to provide a pathway for the passage of other medical devices and/or medicaments, e.g., injectables).

It will be appreciated that, if desired, snare 5 may be mounted to solid shaft rather than a single- or multi-lumen catheter.

Figure 11:
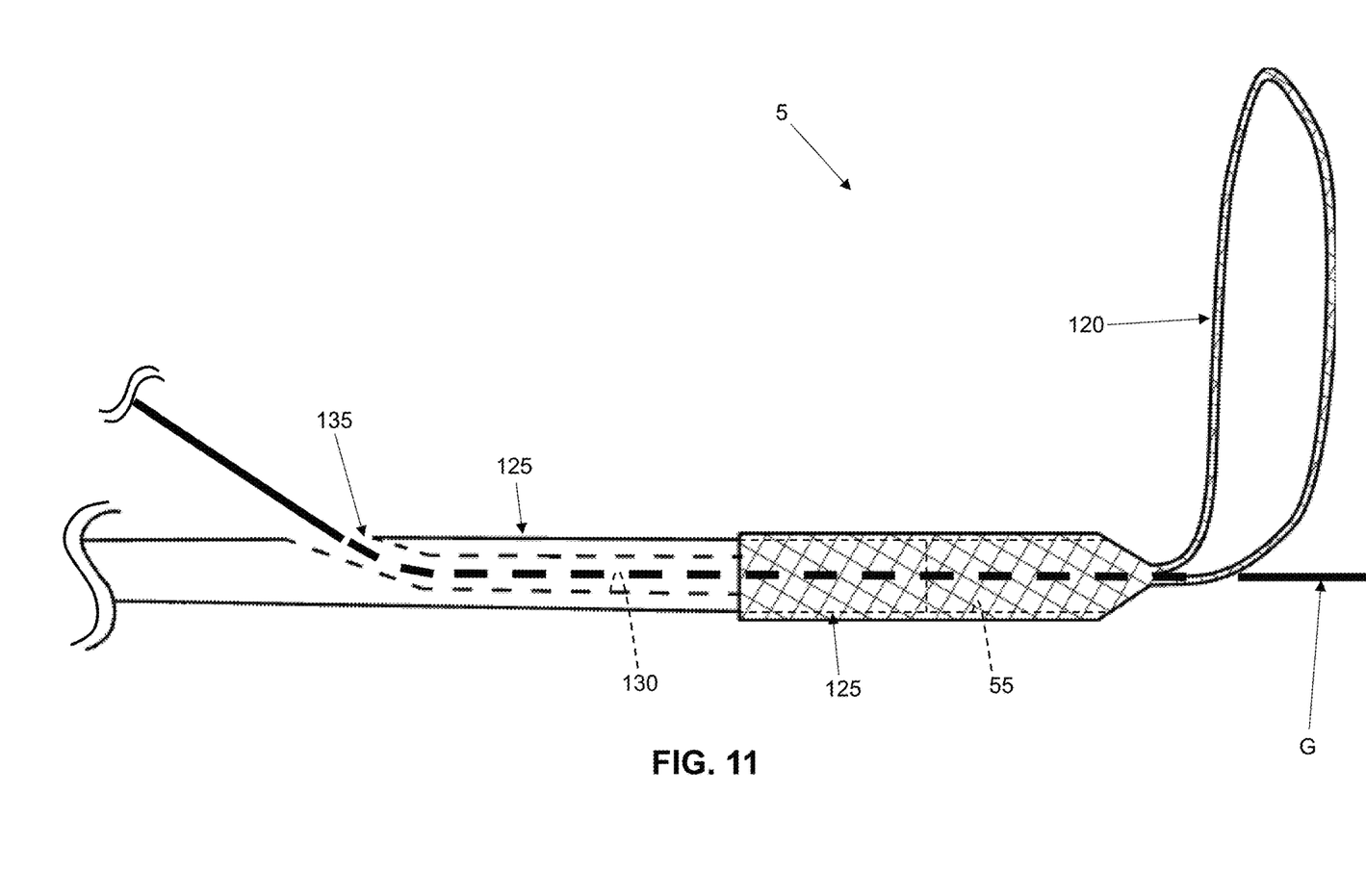
FIG. 11 is a plan view of a novel single-loop snare formed from the novel braided construct of FIGS. 8 and 9 and mounted to a novel catheter formed in accordance with the present invention such that the lumen of the catheter is axially aligned with a guidewire lumen of the novel snare.

In another embodiment of the present invention, and looking now at FIG. 11, snare 5 may be mounted to the distal end of a catheter 125. Catheter 125 is generally similar to the aforementioned catheter 105, however, with catheter 125, the central lumen of the catheter does not extend between the entire length of the catheter. More particularly, catheter 125 is formed with a guidewire lumen 130 that opens on the distal end of catheter 125 and extends proximally to a position distal to the proximal end of catheter 125. A port 135 passes through the sidewall of catheter 125 and opens on guidewire lumen 130, whereby to provide a "quick exchange" side port to accept a guidewire G. It will be appreciated that where snare 5 is to be mounted to the distal end of a catheter (e.g., catheter 105, catheter 125, etc.), a second braided construct (not shown) may be disposed within the central lumen (e.g., central lumen 110) of the catheter, whereby to provide increased strength so as to facilitate movement of the catheter and snare 5 through a tortuous path (e.g., the vasculature of a patient), as will be apparent to one of skill in the art in view of the present disclosure. If desired, heat-bonding may be utilized in order to fuse the second braided construct disposed within the central lumen of the catheter to proximal tube 15 and/or distal tube 20 disposed within central proximal lumen 35 of proximal tube 15, whereby to securely mount snare 5 to the distal end of the catheter.

Figure 12:
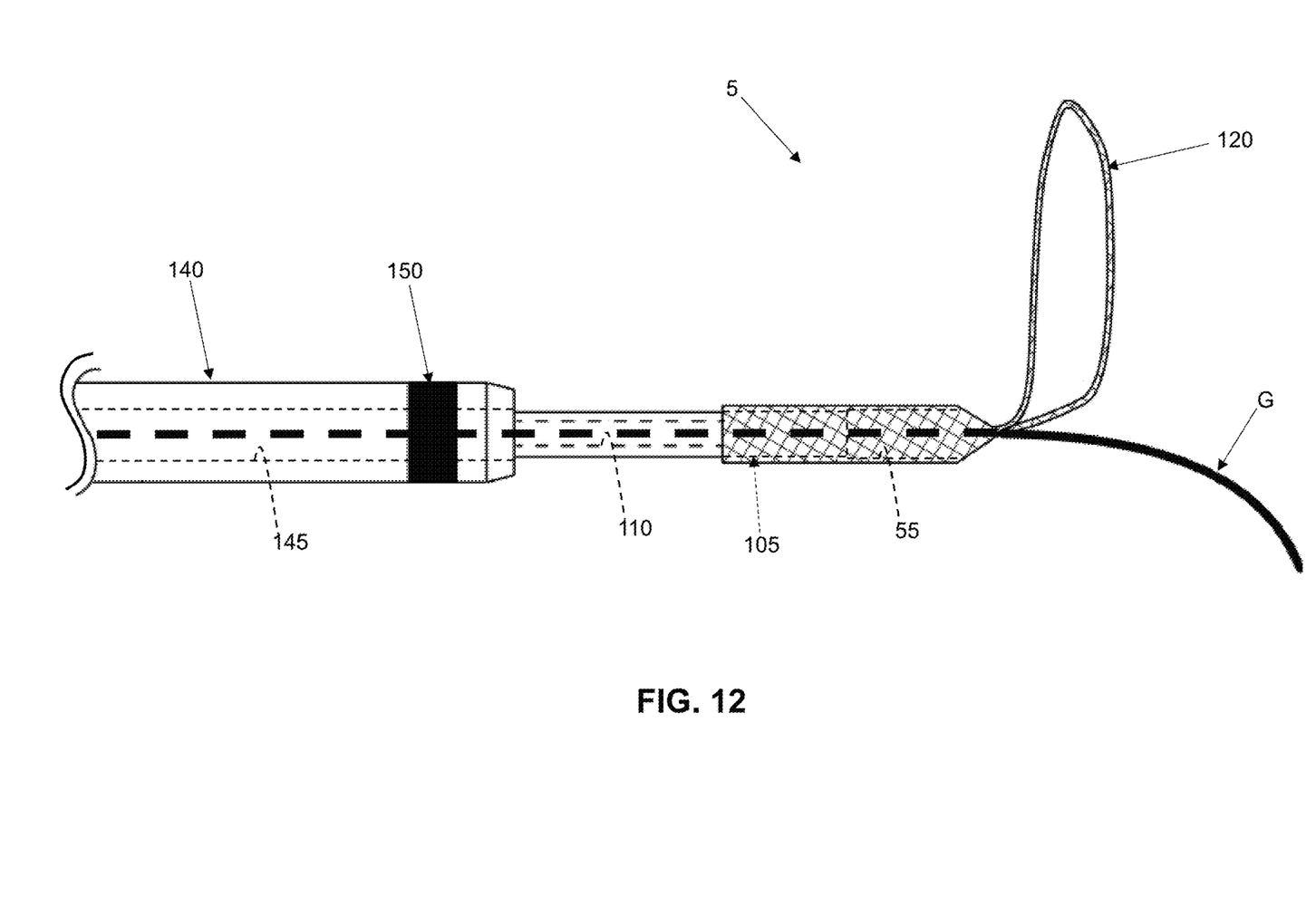
FIG. 12 is a schematic view of a single-loop snare formed from the novel braided construct of FIGS. 8 and 9 mounted to a catheter such that a guidewire lumen of the catheter is axially aligned with a guidewire lumen of the novel snare, and further showing a closing sheath comprising a radiopaque band disposed over the catheter, and a guidewire passing through the snare.

Looking now at FIG. 12, it will also be appreciated that, if desired, a closing sheath 140 may be passed over catheter 105 (or catheter 125) so as to permit an object to be ensnared by single snare loop 120 (or snare loops 90), retracted proximally relative to closing sheath 140, and captured between single snare loop 120 (or snare loops 90) and the distal end of closing sheath 140. More particularly, with this form of the invention, closing sheath 140 generally comprises a distal end, a proximal end, and a lumen 145 extending therebetween. Lumen 145 is sized to slidably receive catheter 105 (or catheter 125) therein, so as to permit closing sheath 140 to move distally/proximally relative to snare 5 (or to permit snare 5 to be moved proximally/distally relative to closing sheath 140). Closing sheath 140 preferably comprises a radiopaque band 145 disposed near the distal end of closing sheath 140, whereby to permit the surgeon to visualize the distal end of closing sheath 140 under image guidance (e.g., fluoroscopy) during a surgical procedure.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for forming a surgical snare, said method comprising:
    providing a plurality of filaments;
    braiding said plurality of filaments together so as to form a braided tubular construct comprising:
        a proximal tube having an open proximal end, an open distal end, and a proximal tube lumen extending there between;
        a distal tube having an open proximal end, an open distal end, and a distal tube lumen extending there between; and
        a loop region disposed between said distal end of said proximal tube and said proximal end of said distal tube, said loop region comprising at least one loop structure, said at least one loop structure comprising at least three of said plurality of filaments braided together;
    inserting said distal end of said distal tube into said open distal end of said proximal tube and into said proximal tube lumen such that (i) said distal tube is disposed in said proximal tube lumen such that said at least one loop structure extends distally of said distal end of said proximal tube in the form of at least one loop, and (ii) said distal tube lumen extends from a point located distal to said proximal end of said proximal tube to said at least one loop.

2. The method according to claim 1 wherein said proximal tube lumen comprises a first radius, said distal tube comprises a second radius, and said second radius is less than said first radius.

3. The method according to claim 1 wherein, when said braided tubular construct is being braided, an external compression sleeve is applied to said distal tube so as to radially constrict said distal tube during braiding.

4. The method according to claim 1 wherein said at least one loop structure comprises a plurality of solid loop structures; and
    wherein, before the step of inserting said distal end of said distal tube into said proximal tube lumen, at least one of said proximal tube and said distal tube is rotated relative to the other of said proximal tube and said distal tube about a central longitudinal axis of said distal tube such that said plurality of solid loop structures are twisted together to form a single solid loop structure.

5. The method according to claim 1 wherein said braided construct is heat annealed after braiding so as to prevent the plurality of filaments from unravelling.

6. The method according to claim 1 wherein each of said plurality of filaments comprises a composite structure comprising:
    a core material; and
    an outer sheath covering said core material.

7. The method according to claim 6 wherein at least one of said core material and said outer sheath comprises a radiopaque material.

8. The method according to claim 7 wherein said core material comprises a noble metal and said outer sheath comprises a shape memory alloy.

9. The method according to claim 8 wherein the shape memory alloy comprises Nitinol, and said core material comprises one selected from the group consisting of gold, platinum, and iridium.

10. The method according to claim 1 wherein each of said plurality of filaments has a diameter of 0.001 inch to 0.008 inch.

11. The method according to claim 1 wherein each of said plurality of filaments is formed from braided or cabled filaments.

12. The method according to claim 1 wherein each of said plurality of loops extends at an angle of between 15 degrees and 90 degrees relative to a longitudinal axis of said distal tube lumen.

13. A surgical snare comprising:
a braided tubular construct formed by braiding together a plurality of filaments, said braided tubular construct comprising:
a proximal tube having an open proximal end, an open distal end, and a proximal tube lumen extending there between;
a distal tube having an open proximal end, an open distal end, and a distal tube lumen extending therebetween; and
a loop region disposed between said distal end of said proximal tube and said proximal end of said distal tube, said loop region comprising a plurality of solid loop structures, each of said plurality of solid loop structures comprising at least three of said plurality of filaments braided together;
wherein said distal end of said distal tube is inserted into said open distal end of said proximal tube and into said proximal tube lumen such that (i) said distal tube is disposed in said proximal tube lumen and said plurality of solid loop structures extend distally of said distal end of said proximal tube in the form of a plurality of loops, and (ii) said distal tube lumen extends from a point located distal to said proximal end of said proximal tube to said plurality of loops.

14. The surgical snare according to claim 13 wherein said surgical snare comprises a single loop formed by rotating at least one of said proximal tube and said distal tube relative to the other of said proximal tube and said distal tube about a central longitudinal axis of said distal tube before said distal tube is inserted into said proximal tube lumen.

15. The surgical snare according to claim 13 wherein said braided construct is heat annealed after braiding so as to prevent the plurality of filaments from unravelling.

16. The surgical snare according to claim 13 wherein each of said plurality of filaments comprises a composite structure comprising:
a core material; and
an outer sheath covering said core material.

17. The surgical snare according to claim 16 wherein at least one of said core material and said outer sheath comprises a radiopaque material.

18. The surgical snare according to claim 17 wherein said core material comprises a noble metal and said outer sheath comprises a shape memory alloy.

19. The surgical snare according to claim 18 wherein the shape memory alloy comprises Nitinol, and said core material comprises one selected from the group consisting of gold, platinum, and iridium.

20. The surgical snare according to claim 13 wherein each of said plurality of filaments has a diameter of 0.001 inch to 0.008 inch.

21. The surgical snare according to claim 13 wherein each of said plurality of filaments is formed from braided or cabled filaments.

22. The surgical snare according to claim 13 wherein each of said plurality of loops extends at an angle of between 15 degrees and 90 degrees relative to a longitudinal axis of said distal tube lumen.

23. The surgical snare according to claim 13 further comprising:
a catheter comprising a distal end, a proximal end, and a sidewall extending therebetween, said sidewall defining a central catheter lumen;
wherein said open proximal end of said proximal tube is mounted to said distal end of said catheter such that said central catheter lumen is axially aligned with said distal tube lumen, and further wherein said central catheter lumen and said distal tube lumen are sized to receive a guidewire therein.

24. The surgical snare according to claim 23 wherein said catheter comprises a port formed in said sidewall of said catheter intermediate said distal end and said proximal end of said catheter, said port opening on said central catheter lumen and sized to receive a guidewire therein.

25. The surgical snare according to claim 23 further comprising a closing sheath comprising a distal end, a proximal end, and a closing sheath lumen extending there between;
wherein said closing sheath lumen is sized to fit over said catheter so as to be slidably moveable relative thereto.

26. The surgical snare according to claim 25 wherein said closing sheath comprises at least one radiopaque band disposed on an outer surface of said closing sheath.

27. A method for forming a surgical snare, said method comprising:
providing twenty-four filaments;
braiding said twenty-four filaments together so as to form a braided tubular construct comprising:
a proximal tube having an open proximal end, an open distal end, and a proximal tube lumen extending there between;
a distal tube having an open proximal end, an open distal end, and a distal tube lumen extending therebetween; and
a loop region disposed between said distal end of said proximal tube and said proximal end of said distal tube, said loop region comprising three solid loop structures, each of said three solid loop structures comprising eight filaments braided together;
radially constraining said distal tube during braiding of said distal tube such that said distal tube comprises a radius that is less than the radius of said distal tube lumen;
inserting said distal end of said distal tube into said open distal end of said proximal tube and into said proximal tube lumen such that (i) said distal tube is disposed in said proximal tube lumen and said three solid loop structures extend distally of said distal end of said proximal tube in the form of three loops, and (ii) said distal tube lumen extends from a point located distal to said proximal end of said proximal tube to said three loops.

28. A method for forming a surgical snare, said method comprising:
providing a plurality of filaments;
braiding said plurality of filaments together so as to form a braided tubular construct comprising:
a proximal tube having an open proximal end, an open distal end, and a proximal tube lumen extending there between;
a distal tube having an open proximal end, an open distal end, and a distal tube lumen extending therebetween; and
a loop region disposed between said distal end of said proximal tube and said proximal end of said distal tube, said loop region comprising a plurality of solid loop structures, each of said plurality of solid loop structures comprising at least three of said plurality of filaments braided together;

rotating at least one of said proximal tube and said distal tube relative to the other of said proximal tube and said distal tube about a central longitudinal axis of said distal tube such that said plurality of solid loop structures are twisted together to form a single solid loop structure;

inserting said distal end of said distal tube into said open distal end of said proximal tube and into said proximal tube lumen such that (i) said distal tube is disposed in said proximal tube lumen and said single solid loop structure extends distally of said distal end of said proximal tube, and (ii) said distal tube lumen extends from a point located distal to said proximal end of said proximal tube to said single solid loop structure.

* * * * *